United States Patent
Roessl et al.

(10) Patent No.: US 9,839,407 B2
(45) Date of Patent: Dec. 12, 2017

(54) CORRECTION IN SLIT-SCANNING PHASE CONTRAST IMAGING

(71) Applicant: KONINKLIJKE PHILIPS N.V., Eindhoven (NL)

(72) Inventors: Ewald Roessl, Henstedt-Ulzburg (DE); Gerhard Martens, Henstedt-Ulzburg (DE)

(73) Assignee: Koninklijke Philips N.V., Eindhoven (NL)

( * ) Notice: Subject to any disclaimer, the term of this patent is extended or adjusted under 35 U.S.C. 154(b) by 167 days.

(21) Appl. No.: 14/896,783

(22) PCT Filed: Jun. 27, 2014

(86) PCT No.: PCT/EP2014/063679
§ 371 (c)(1),
(2) Date: Dec. 8, 2015

(87) PCT Pub. No.: WO2014/207193
PCT Pub. Date: Dec. 31, 2014

(65) Prior Publication Data
US 2016/0128665 A1    May 12, 2016

(30) Foreign Application Priority Data

Jun. 28, 2013    (EP) .................................... 13174345

(51) Int. Cl.
*A61B 6/03*    (2006.01)
*A61B 6/00*    (2006.01)
(Continued)

(52) U.S. Cl.
CPC .............. *A61B 6/582* (2013.01); *A61B 6/484* (2013.01); *A61B 6/5258* (2013.01); *A61B 6/583* (2013.01);
(Continued)

(58) Field of Classification Search
CPC .. G21K 1/04; G21K 1/06; G21K 1/02; G21K 1/025; A61B 6/06; A61B 3/102; A61B 6/582; A61B 6/583; A61N 5/1045
(Continued)

(56) References Cited

U.S. PATENT DOCUMENTS

| | | |
|---|---|---|
| 2011/0243305 A1 | 10/2011 | Tada |
| 2012/0099702 A1 | 4/2012 | Engel et al. |

(Continued)

FOREIGN PATENT DOCUMENTS

| | | |
|---|---|---|
| WO | 2012/080900 | 6/2012 |
| WO | 2013/004574 | 1/2013 |

OTHER PUBLICATIONS

"McNichols Fiberglass for Pool Drain Safety", Jun. 4, 2012 (Jun. 4, 2012), pp. 1-3, XP055073945.

(Continued)

*Primary Examiner* — Don Wong

(57) ABSTRACT

The present invention relates to calibration in X-ray phase contrast imaging. In order to remove the disturbance due to individual gain factors, a calibration filter grating (10) for a slit-scanning X-ray phase contrast imaging arrangement is provided that comprises a first plurality of filter segments (11) comprising a filter material (12) and a second plurality of opening segments (13). The filter segments and the opening segments are arranged alternating as a filter pattern (15). The filter material is made from a material with structural elements (14) comprising structural parameters in the micrometer region. The filter grating is movably arranged between an X-ray source grating (54) and an analyzer grating (60) of an interferometer unit in a slit-scanning system of a phase contrast imaging arrangement. The slit-scanning system is provided with a pre-collimator (Continued)

(55) comprising a plurality of bars (57) and slits (59). The filter pattern is aligned with the pre-collimator pattern (61).

14 Claims, 8 Drawing Sheets

(51) Int. Cl.
*G01N 23/20* (2006.01)
*G21K 1/06* (2006.01)
*G21K 1/10* (2006.01)
*G02B 5/18* (2006.01)

(52) U.S. Cl.
CPC ......... *G01N 23/20075* (2013.01); *G21K 1/06* (2013.01); *G21K 1/10* (2013.01); *G01N 2223/303* (2013.01); *G02B 5/1838* (2013.01); *G21K 2207/005* (2013.01)

(58) Field of Classification Search
USPC ... 378/147, 156, 149, 154, 157, 158, 85, 16, 378/155, 207
See application file for complete search history.

(56) References Cited

U.S. PATENT DOCUMENTS

| | | |
|---|---|---|
| 2012/0155610 A1 | 6/2012 | Murakoshi |
| 2012/0243658 A1* | 9/2012 | Geller ............. A61B 6/00 378/16 |
| 2012/0250823 A1 | 10/2012 | Vogtmeier |
| 2013/0094625 A1 | 4/2013 | Huang |

OTHER PUBLICATIONS

C David et al: "Fabrication of diffraction gratings for hard X-ray phase contrast imaging", Microelectronic Engineering, vol. 84, No. 5-8, May 1, 2007 (May 1, 2007), pp. 1172-1177, XP05500153.

* cited by examiner

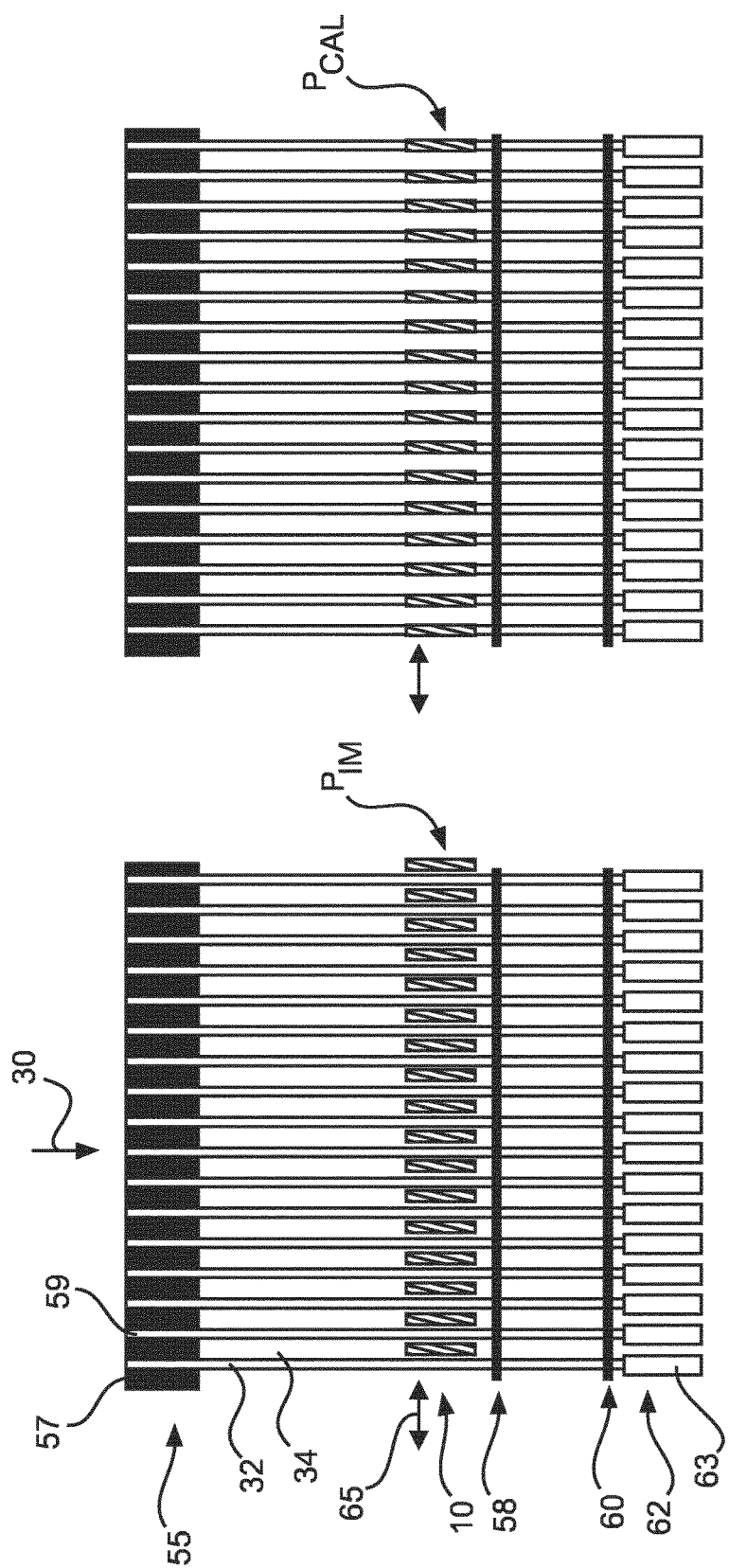

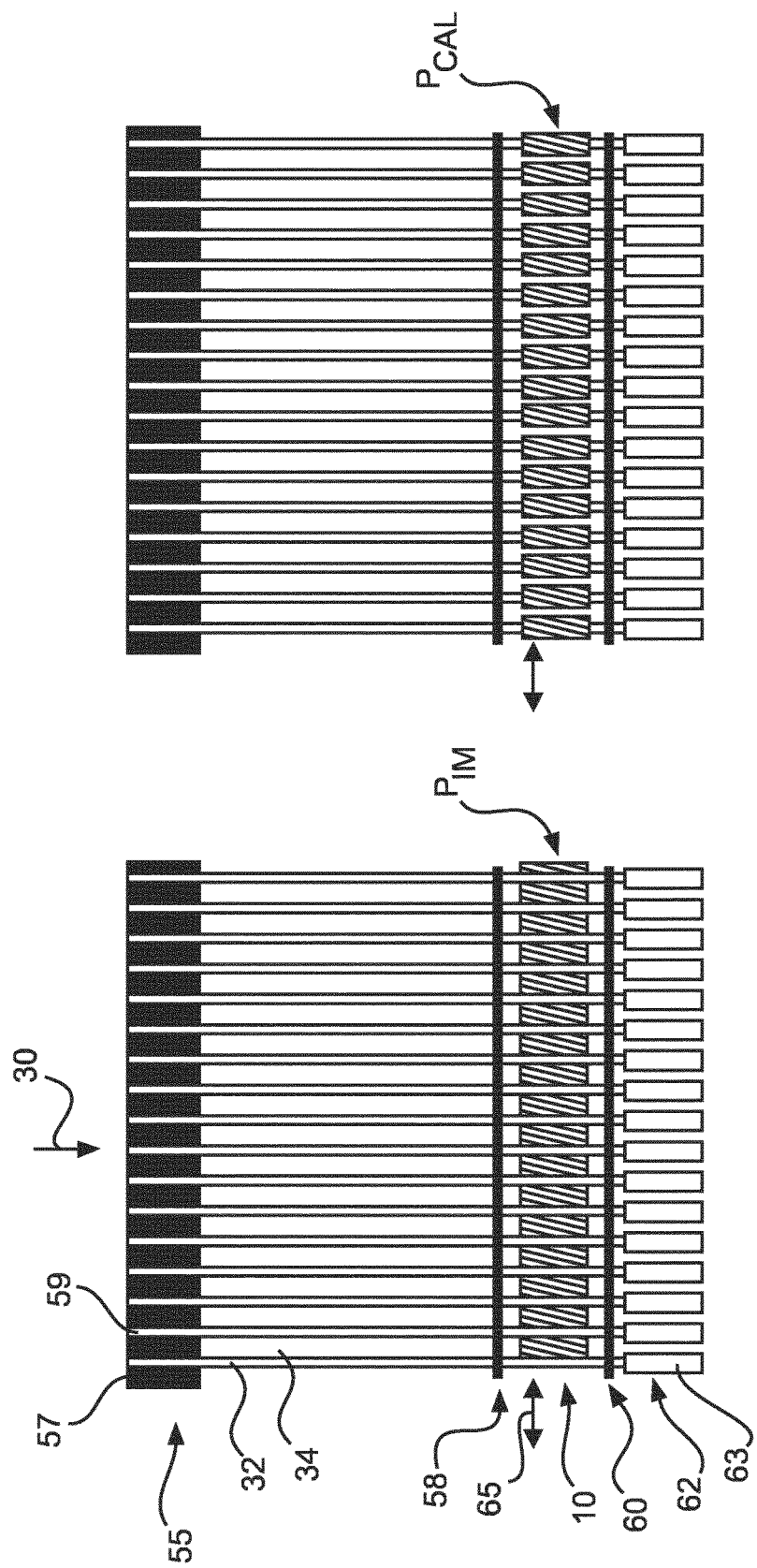

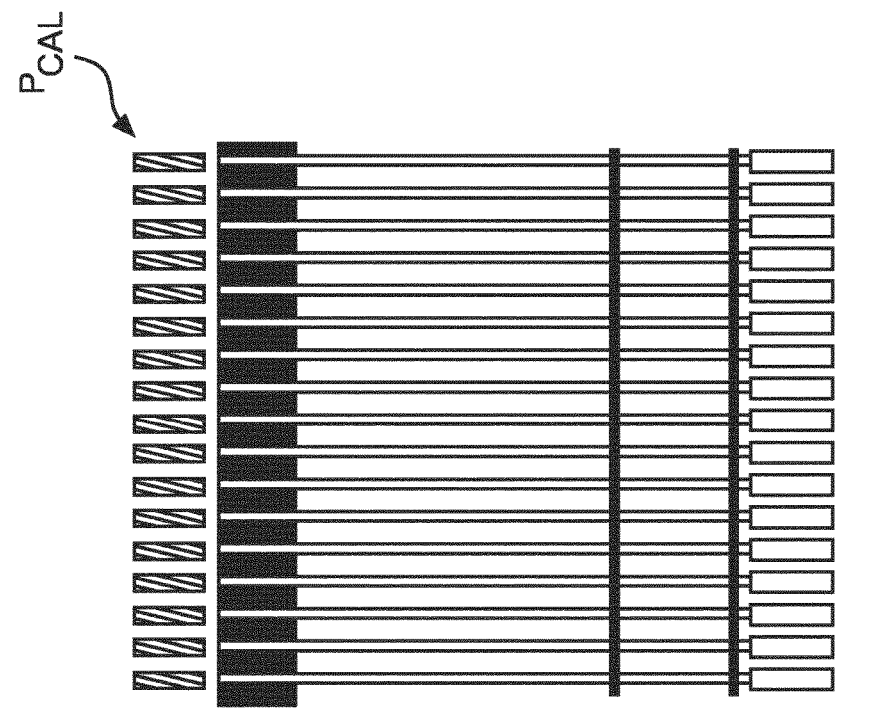
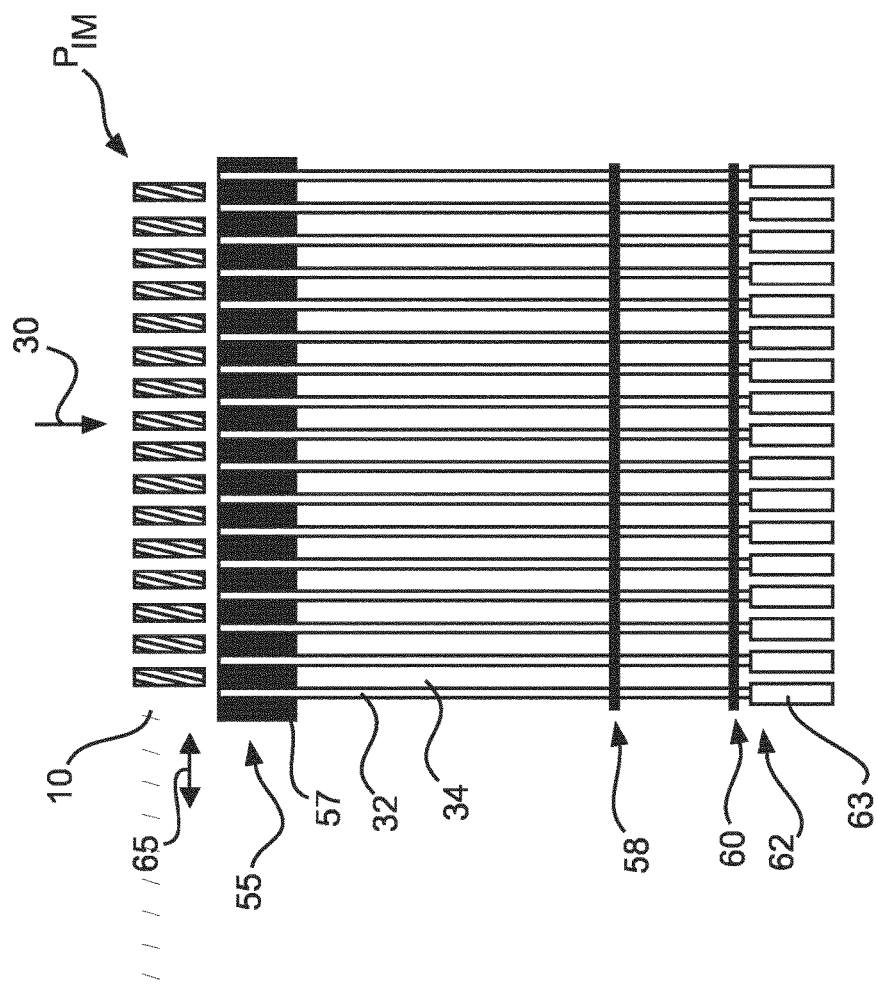

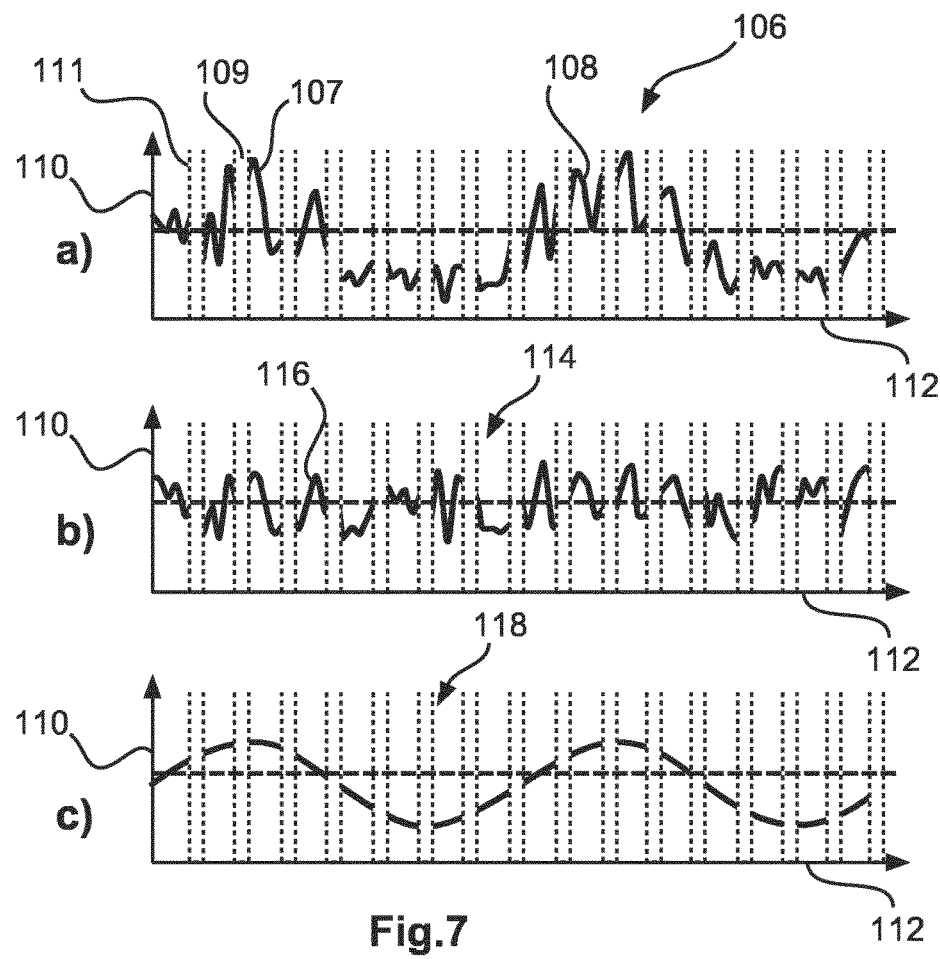
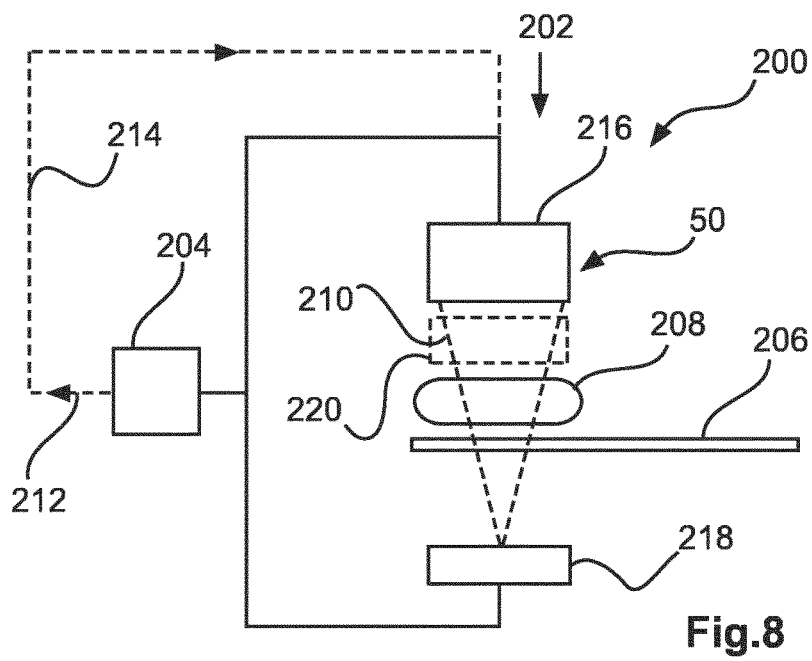

CORRECTION IN SLIT-SCANNING PHASE CONTRAST IMAGING

CROSS REFERENCE TO RELATED APPLICATIONS

This application is a national filing of PCT application Serial No. PCT/EP2014/063679, filed Jun. 27, 2014, published as WO 2014/207193 on Dec. 31, 2014, which claims the benefit of European Application Number 13174345.2 filed Jun. 28, 2013, which is incorporated herein by reference.

FIELD OF THE INVENTION

The present invention relates to calibration in slit-scanning X-ray phase contrast imaging, and relates in particular to a calibration filter grating for a slit-scanning X-ray phase contrast imaging arrangement, to a slit-scanning X-ray phase contrast imaging arrangement, to an X-ray imaging system, and to a method for calibration in slit-scanning X-ray phase contrast imaging, as well as to a computer program element and a computer-readable medium.

BACKGROUND OF THE INVENTION

For phase contrast imaging based on slit-scanning, for example for differential phase contrast imaging (DPCI), a required pre-processing step is flat field correction in the imaging applications. DPCI is an emerging technology that has the potential to improve the diagnostic value of X-ray imaging. A DPCI system may be provided with three gratings used between the X-ray source and the detector. The acquisitions of several X-ray images at different relative positions of two of the gratings close to the detector are required. Since these gratings have pitches in the order of a few micrometers only, there are tight requirements on the accuracy of the stepping device that performs the relative movement of the gratings. For example, U.S. 2012/0099702 A1 describes a correction method for differential phase contrast imaging. Furthermore, U.S. 2011/243305 A1 discloses a system for X-ray phase contrast imaging as well as a phantom for sensitivity correction of such system. In addition, WO 2013/004574 A1 discloses a slit scanning system for generating X-ray phase contrast images. Further, for a large object, a large field of view is necessary in case the object has to be imaged by a single phase stepping series. Alternatively, systems may be used with a small field of view, but in addition a scan of the object relative to the imaging system may be provided. Either the imaging system is moved relative to the object, or the object is moved with respect to a fixed imaging system. A prerequisite is that a phase shift of at least one interference fringe period of the interferometer occurs. However, the fringe profile achieved may not look like the ideal fringe pattern. It has been shown that due to the internal electrical gains, as well as due to individual pixel surface areas, the individual detective quantum efficiencies and the individual X-ray transmission factors of the system, the detected fringe distribution shows up being systematically disturbed.

SUMMARY OF THE INVENTION

There may thus be a need to remove the disturbance due to individual gain factors in a slit-scanning system.

The object of the present invention is solved by the subject-matter of the independent claims, wherein further embodiments are incorporated in the dependent claims. It should be noted that the following described aspects of the invention apply also for the calibration filter grating for a slit-scanning X-ray phase contrast imaging arrangement, for the slit-scanning X-ray phase contrast imaging arrangement, for the X-ray imaging system, and for the method for calibration in slit-scanning X-ray phase contrast imaging, as well as for the computer program element and the computer-readable medium.

According to the present invention, a calibration filter grating for a slit-scanning X-ray phase contrast imaging arrangement is provided. The calibration filter grating comprises a first plurality of filter segments comprising a filter material, and a second plurality of opening segments. The filter segments and the opening segments are arranged alternating as a filter pattern. The filter material is made from a material with structural elements comprising structural parameters in the micrometer region. The filter grating is configured to be movably arranged between an X-ray source grating and an analyzer grating of an interferometer unit in a slit-scanning system of a phase contrast imaging arrangement. The filter pattern is configured to be aligned with a slit pattern of the slit-scanning system.

This allows removing the gain induced disturbance of the Moiré fringe distribution by referencing the pixel output to a flat field referencing image. The flat field reference image in a differential phase contrast imaging setup provides the removal of the Moiré fringes without having to detune the interferometer setup. In particular, the calibration filter grating according to the present invention avoids the detuning of the interferometer setup and in particular the removal of significant parts. The calibration filter grating provides a removal of the coherent part of the X-ray radiation provided by the primary grating (grating G0) before the X-ray flux is passing the interferometer gratings in form of the phase grating (grating G1) and the analyzer grating (grating G2). The coherent part is transformed by the filter into incoherent X-rays before the X-rays enter the interferometer, or in case of an arrangement of the filter between G1 and G2—before the X-rays enter the analyzer grating of the interferometer. As an effect, the filter material with the structural elements comprises structural parameters in the micrometer region, random small angle scattering is provided. Therefore, the filter material has dark field property, which causes the de-coherence of the X-rays passing the material. The arrangement of the calibration filter as a coarse grating provides the advantage that the filter can remain arranged in an imaging system, i.e. in the path of the X-ray beam, since the bars of the filter are movable to be aligned either with the bars of the device, e.g. a pre-collimator, splitting the X-ray beam into a number of X-ray strips, for slit-scanning imaging, or aligned with openings of the device splitting X-ray beam, for calibrating.

The term "slit-scanning" refers to X-ray imaging with a plurality of strip-like beam portions radiated towards a detector that is configured as a plurality of respectively arranged strip-like detector portions. An example of such slit-scanning system is the MicroDose® mammography system from Philips®.

The term "structural parameters" relates to a change in structural properties in the given range.

The term "micrometer" relates to a size that is best described using the unit micrometer to avoid fractions of a unit, or values with number positions following, i.e. behind the decimal point. For example, "micrometer" relates to a size the smaller than 1 mm (millimeter), e.g. smaller than 1000 μm (micrometer), for example smaller than 0.1 mm, i.e. smaller than 100 μm.

For example, as long as the coherent part of the X-ray radiation has not been demodulated by the analyzer grating (G2), the coherence of the X-rays can still be removed by a de-coherence filter arranged behind the phase grating (G1). As an advantage, the arrangement between the source grating (G0) and the phase grating (G1), avoiding an arrangement of the filter in the interferometer between the phase grating (G1) and the analyzer grating (G2), also considers space and efficiency aspects.

For example, the opening segments are filled with air. In another example, an X-ray transparent and X-ray non-scattering filter material is provided for the opening segments.

According to an example, the structural elements are provided in a maximum range of 10 μm.

According to an example, the filter material is provided as fluid bubbles comprising gaseous bubbles and/or liquid bubbles.

According to an example, the filter material is provided as fiber-based materials.

In these examples, the filter material is made from low atomic number elements. The term "low atomic number elements" relates to material with a maximum value of approximately $C_{max} \approx 20$.

The gaseous bubbles may be provided as air bubbles or gas bubbles. The fiber-based material may be made from wood, paper, tissue-fabrics and mineral wool, or others with random orientation of fibers or with highly-oriented fibers.

In an example, the filter material is provided with a thickness in the range of approximately 5 to 100 mm.

In another example, the structural parameters of the filter materials are close to the grating period of the grating G1.

According to an example, the filter is a de-coherence filter providing small angle scattering for coherent X-ray radiation provided by an X-source with a source grating for phase contrast imaging.

The term "small angle scattering" refers to a scattering in an angle range of smaller than about 1 micro-rad.

In an example, the X-ray radiation is attenuated and also refracted minimally.

According to the invention, also a slit-scanning X-ray phase contrast imaging arrangement is provided that comprises an X-ray source, a source grating, a pre-collimator, an interferometer unit with a phase grating and an analyzer grating, an X-ray detector with a plurality of detector segments displaced from each other, and a calibration device (64). The source grating provides at least partially coherent X-ray radiation. The pre-collimator comprises a plurality of bars and slits to provide an X-ray beam width with a plurality of X-ray beam sections displaced from each other by radiation-free sections. The calibration device is a calibration filter grating according to one of the preceding examples. Further, the calibration filter grating is arranged between the source grating and the analyzer grating. The calibration filter grating is movable between:
  I) a first, calibrating position, in which the filter segments are arranged in the X-ray beam parts forming the plurality of X-ray beam sections; and
  II) a second, scanning position, in which the filter segments are arranged out of the X-ray beam parts forming the plurality of X-ray beam sections that are detected by the detector segments.

As an advantage, an X-ray phase contrast imaging arrangement is provided that can be calibrated in particular with respect to identifying and removing disturbance in the Moiré pattern due to individual gain factors. The imaging arrangement can advantageously be provided in a compact manner. Since the calibration filter grating needs to be moved only in the amount of half the pitch of the filter grating structure, the filter grating can be provided in an integrated manner leading to a facilitated design with increased compatibility with respect to other equipment in an examination room.

In the first, calibrating position, the filter segments are arranged in the X-ray beam parts forming the plurality of X-ray beam sections such that the radiation forming the beam sections pass through the filter material over their complete width. In the second, scanning position, the filter segments are arranged out of the X-ray beam parts forming the plurality of X-ray beam sections such that the radiation forming the beam sections pass towards the detector through the opening segments. The scanning position is also referred to as normal operation mode.

According to an example, the calibration filter grating is arranged:
  i) between the source grating and the pre-collimator; or
  ii) between the pre-collimator and the phase grating; or
  iii) between the phase grating and the analyzer grating.

In an example, in the arrangement according to i) the distance of the filter to the detector is larger than in the arrangements according to ii) or iii). An increasing distance may reduce the filter effect, but in example this is compensated by an increase in the filter thickness. In an example, a filter material of 5 mm thickness is arranged in front of the phase grating or between the phase grating and the analyzer grating, wherein the filter provides sufficient destruction or reduction of the coherence.

In an example, the filter, in addition to removing interferences, also attenuates the beam homogenously for all pixels. Otherwise a random attenuation profile of the filter may be interpreted as gain variations during the gain calibration with the filter in the beam. Thus, the filter is made homogeneously macroscopically for homogeneous attenuation, but inhomogeneous on the micrometer scale for providing de-coherence.

In another example, the same (or similar) filter material is provided with 10 mm thickness when arranged in front of the pre-collimator.

For example, the filter is provided integrated within the frame or housing of the pre-collimator.

According to an example, the phase grating is provided with a first period, and the structures of the structural elements of the filter material are provided in a range of approximately the first period.

The term "approximately" refers to a range of about 30 to 300% of the given value of the first period of the phase grating.

According to an example, the calibration filter grating is arranged with a calibration distance of approximately 5 to 10 mm from the phase grating. In an example, the calibration filter grating is arranged half distance between the X-ray source grating G0 and the phase grating G1. The "filter" strength may then be reduced to approximately half the amount, but this may be compensated by the double filter thickness, but also intrinsic absorption is enhanced.

According to an example, a displacement device for moving the calibration filter grating between the first, calibrating position and the second, scanning position is provided.

The displacement device is also referred to as movement device.

In an example, the displacement device is provided as at least one of the group of a motor driven translation stage, a electromagnetic actuation stage, and a piezoelectric translation stage.

According to the invention, also an X-ray imaging system is provided that comprises an X-ray image acquisition arrangement, a processing device, and an object supporting device. The X-ray image acquisition arrangement is provided as a slit-scanning X-ray phase contrast imaging arrangement according to one of the above-mentioned examples. The object supporting device is configured to support an object to be examined. Further, the X-ray image acquisition arrangement is configured to detect an X-ray image signal as reference signal for calibration purposes, while an object is arranged outside the X-ray radiation. The processing unit is configured to determine a calibration factor based on the reference signal, wherein the calibration factor represents a gain induced signal structure. The processing unit is further configured to provide the calibration factor for calibrated X-ray imaging procedures.

As an advantage, an imaging system is provided that can be calibrated in a routine manner and also on demand. This results in an increased image quality due to improved image data and thus supports the analytical and diagnostic procedures performed by a doctor or other clinical staff.

According to an example, the filter segments of the calibration device are configured to be arranged in the X-ray beam parts forming the X-ray beam sections for calibration purposes and outside the X-ray beam parts forming the X-ray beam sections for object and phase reference acquisition steps.

For example, in case of the arrangement according to i), the filter segments of the calibration device are arranged in the X-ray beam parts that will pass pre-collimator slits to form the X-ray beam sections for calibration purposes, and outside those X-ray beam parts for object and phase reference acquisition steps.

For example, in case of the arrangement according to ii) and iii), the filter segments of the calibration device are arranged in the X-ray beam sections for calibration purposes, and outside the X-ray beam sections for object and phase reference acquisition steps.

In an example, the system is configured to provide three scans:
   i) scan without object and without filter;
   ii) scan with filter only; and
   iii) scan with object only.

According to the invention, also a method for calibration in slit-scanning X-ray phase contrast imaging is provided. The method comprises the following steps:
   a) arranging a first plurality of filter segments of a calibration filter in X-ray beam parts forming X-ray beam sections of an X-ray image acquisition arrangement at a location between a source grating and an analyzer grating; wherein the filter segments comprise a filter material made from a material with structural elements comprising structural parameters in the micrometer region;
   b) providing X-ray radiation;
   c) detecting an X-ray image signal as reference signal for calibration purposes;
   d) determining a calibration factor based on the reference signal, wherein the calibration factor represents a gain induced signal structure; and
   e) providing the calibration factor for calibrated X-ray imaging procedures.

For example, in step e), the calibration factor is used to remove gain induced disturbances in next image acquisition steps.

In an example, the steps a) to d) are repeated before an object is arranged for a new image acquisition procedure.

According to the invention, the Moiré fringe pattern resulting from the coherent X-ray radiation is temporarily suppressed by temporarily inserting a special filter grating into the X-ray path that cancels the coherence and thus the interference capability of the X-rays. The provision of a filter grating provides the effect that the filter does not need to be removed out of the radiation beam, but only needs to be moved laterally such that the bars of the filter grating are aligned with the slit arrangement of the pre-collimator, i.e. the filter grating bars are aligned with the slits of the pre-collimator for calibration scanning and for slit-scanning, the filter grating bars are aligned with the bars of the pre-collimator. In an example, lightweight material with internal microstructures is provided, wherein the dimensions of the microstructures may be close to the pitch of the interferometer grating. Thus, a flat field reference image can be acquired, which can then be used for calibration purposes. The movement and thus insertion of the de-coherence flat field filter grating into the parts of the X-ay beam that hit the detector portions may be done manually by hand or motor-driven, and computer-controlled by a translation stage. The special filter grating can be arranged in between the source grating and the G2 grating of the interferometer unit. Its preferable position with respect to available space and efficiency is just in front of the interferometer unit, or also just in front of the pre-collimator.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIG. 3 shows an example of a schematic setup of a slit-scanning X-ray phase contrast imaging arrangement in an imaging position in FIG. 3A and in a calibration position in FIG. 3B;

FIG. 4 shows a further example of a setup of a slit-scanning X-ray phase contrast imaging arrangement in an imaging position in FIG. 4A and in a calibration position in FIG. 4B;

FIG. 5 shows another example of a setup of a slit-scanning X-ray phase contrast imaging arrangement in an imaging position in FIG. 5A and in a calibration position in FIG. 5B;

FIG. 7 shows detector signal distribution for a scan without flat field correction in FIG. 7A), a scan in the presence of a de-coherence flat filter in FIG. 7B), and the ratio of detector signal versus the flat field reference signal in FIG. 7C);

FIG. 8 shows a schematic setup of an example of an X-ray imaging system; and

DETAILED DESCRIPTION OF EMBODIMENTS

Figure 1A:
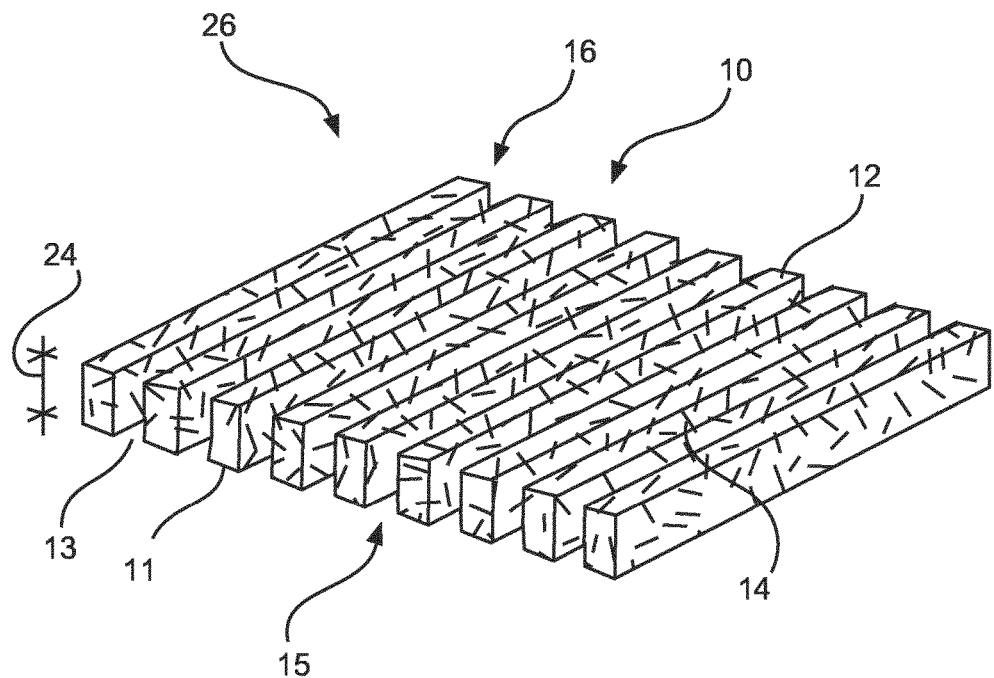
FIG. 1A shows a perspective view of an example of a calibration filter grating.

FIG. 1A shows a calibration filter grating 10 for an X-ray phase contrast imaging arrangement. The calibration filter grating 10 comprises a first plurality of filter segments 11 comprising a filter material 12. The filter material 12 is made from a material with structural elements 14, which are only schematically indicated in FIG. 1A without being to scale, comprising structural parameters in the micrometer region. Further, second plurality of opening segments 13 is provided. The filter segments 11 and the opening segments 13 are arranged alternating as a filter pattern 15. The calibration filter grating 10 is configured to be movably arranged between an X-ray source grating and an analyzing grating of an interferometer unit in a slit-scanning system of a phase contrast imaging arrangement, which will also be explained in more detail in relation with FIGS. 2 to 6. The filter pattern 15 is configured to be aligned with a slit pattern of the slit-scanning system (see also below).

Figure 1B:
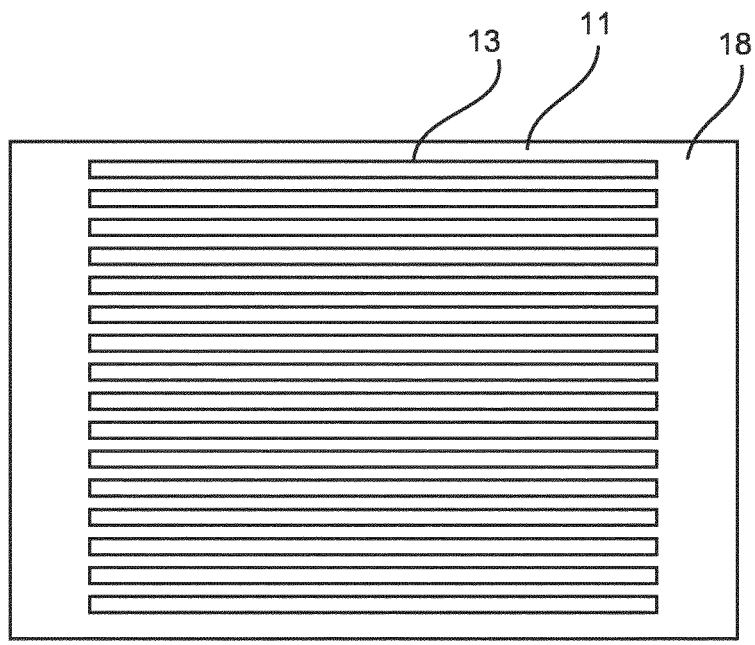
FIG. 1B shows a top view of a further example of a calibration filter grating.

The filter material 12, i.e. the filter segments 11 are shown as a grid-like arrangement 16 of the filter material in FIG. 1A. In another example, shown in FIG. 1B in a top view, the filter segments are provided as a grid with frame portions 18.

The filter material 12 may also be arranged in a grid-like support construction (not further shown), such as in housing parts or frame parts. The structural elements 14 are provided in a maximum range of 10 μm.

As a material with the structural parameters in the micrometer region, materials with strong de-coherent properties are provided, such as: a) air or gas bubbles-based material, such as industrial foams, for example Styrofoam® and Rohacell® or polyurethane-based foams; b) liquid- 'bubble'- or powder-based material, such as oil/water-emulsions or liquid-based polishing agents. In a further example, flour- or dust-based materials are provided as standalone material or embedded in a rigid matrix; c) fiber-based material, such as food, paper, tissue/fabrics and mineral wool, etc., which can be provided either with random orientation of fibers up to highly-oriented ones; and/or d) special kinds of rubber materials, such as some eraser materials or cork.

When choosing a filter material containing only low atomic number elements, the X-ray attenuation will be very low, even in X-ray mammography imaging for example. The restriction provided is that a homogenous and flat filter can be inserted into the X-ray path. For example, a rigid flat filter is provided, or an emulsion or liquid in a provided container. The temporarily insert of the de-coherence filter into the X-ray beam may be provided by hand or motor-driven, or computer-controlled by a translation stage.

In an example, the filter material 12 is provided as fiber-based material, wherein the filter material 12 is made from low atomic number elements. For example, the filter material 12 is made from a material with a maximum value of approximately $C_{max} \approx 20$.

In a further example, the filter material 12 is provided as an industrial foam, such as Styrofoam®, Rohacell®, Zotek®, Kynar® or others (not further shown).

In a still further example, a lightweight material, such as wood or paper, or a tissue or fabric, is provided with internal microstructures (not further shown).

According to an example, the filter material 12 is provided with a thickness 24 in the range of approximately 5 to 100 mm.

According to a further example, also shown in FIG. 1A, the calibration filter grating 10 is a de-coherence filter 26, providing small angle scattering for coherent X-ray radiation provided by an X-source with a source grating for phase contrast imaging. In a further example of the calibration filter grating 10 (not shown), the filter material 12 is provided as fluid bubbles. The fluid bubbles are provided by a grid-structured housing, for example a frame with enclosing sidewalls, enclosing the filter material 12. The fluid bubbles may be provided as gaseous bubbles and/or liquid bubbles.

Figure 2:
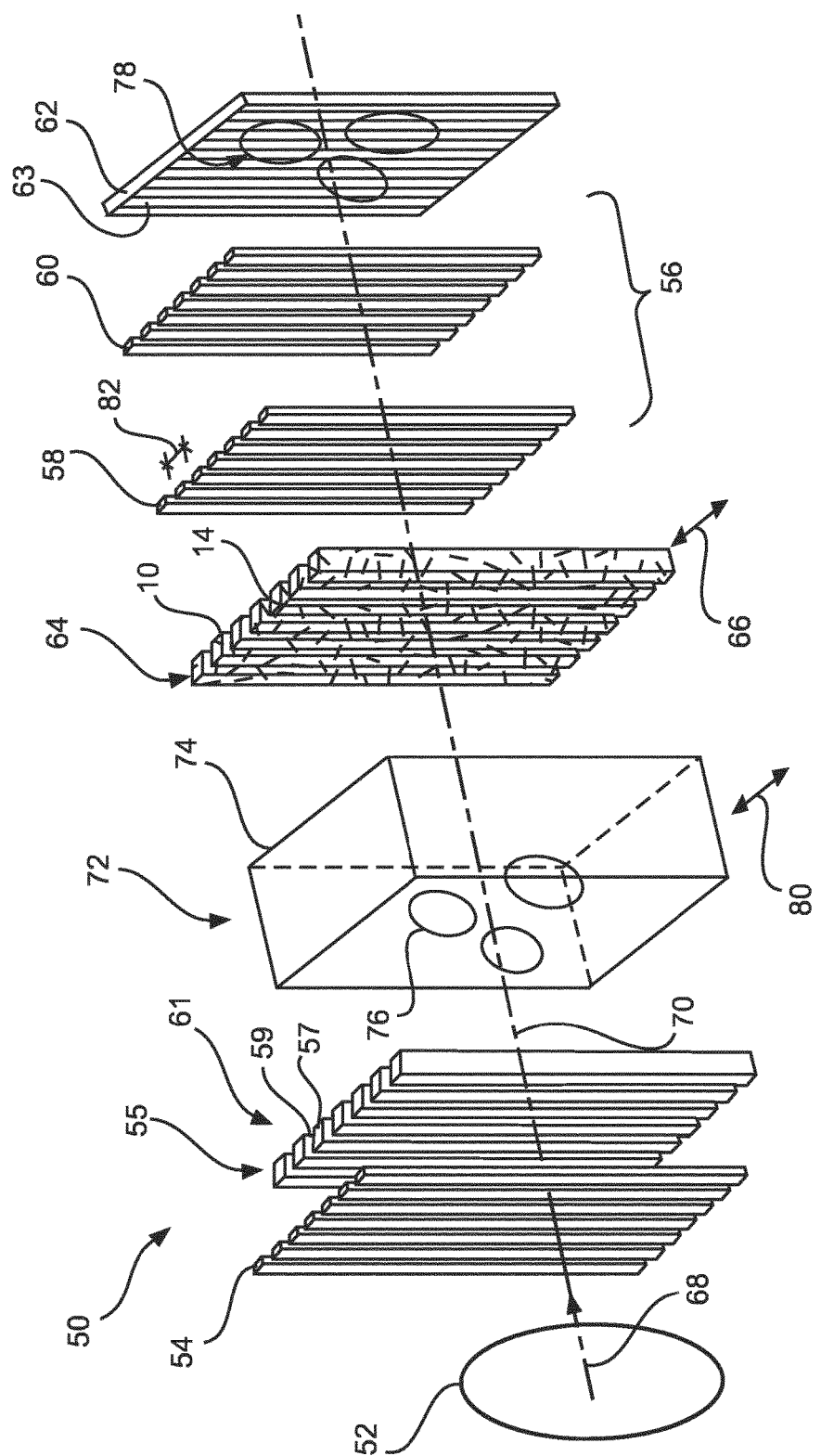
FIG. 2 shows a schematic setup of a slit-scanning X-ray phase contrast imaging arrangement in an example.

FIG. 2 shows a slit-scanning X-ray phase contrast imaging arrangement 50, comprising an X-ray source 52, a source grating 54 (also referred to as grating G0), a pre-collimator 55, an interferometer unit 56 comprising a phase grating 58 (grating G1) and an analyzer grating 60 (grating G2). The pre-collimator comprises a plurality of bars 57 and slits 59 to provide an X-ray beam width with a plurality of X-ray beam sections displaced from each other by radiation-free sections. The bars 57 and slits thus provide a pre-collimator pattern 61. Further, an X-ray detector 62 with a plurality of detector segments 63 displaced from each other is provided. Still further, a calibration device 64 is provided as the calibration filter grating 10 according to one of the above-mentioned examples. The calibration filter grating 10 is arranged between the source grating 54 and the analyzer grating 60, for example between the source grating 54 and the interferometer unit 56. The calibration filter grating 10 is movable between a first, calibrating position, in which the filter segments are arranged in the X-ray beam parts forming the plurality of X-ray beam sections; and a second, scanning position, in which the filter segments are arranged out of the X-ray beam parts forming the plurality of X-ray beam sections that are detected by the detector segments. This is further explained in relation with FIGS. 3 to 5. The lateral movement of the calibration filter grating 10 is indicated with a first arrow 66. Alternatively, the calibration filter grating 10 is arranged in the interferometer between the phase grating 58 (grating G1) and the analyzer grating 60 (grating G2), or in front of the pre-collimator 55, i.e. between the source grating 54 and the pre-collimator 55.

The X-ray source 52 generates incoherent X-ray radiation 68. The X-ray radiation passes the source grating 54 and thus becomes at least partially coherent X-ray radiation 70. The coherent X-ray radiation 70 then passes the pre-collimator 55 to provide the plurality of X-ray beam sections and then travels along a region 72 that is provided to receive an object 74 towards the phase grating 58 and the analyzer grating 60, and finally hits the detector 62.

The object 74 may be provided with structures 76 which will be projected by the coherent X-ray radiation 70 on the detector 62, which is indicated with the similar structure 78. However, it must be noted that the detected structure 78 is provided after evaluating the detector signals.

For calibration purposes, the object 74 is removed from the region 72, and will be arranged in the region 72 after the calibration scan, as indicated with a second arrow 80.

The phase grating 58 is provided with a first period 82 and the structures of the structural elements 14 are provided in a range of approximately the first period. The structures are provided in a range of about 30 to 300 percent of the value of the first period 82.

In FIGS. 3 to 5, different examples for a setup of the slit-scanning X-ray phase contrast imaging arrangement 50 are schematically shown. In FIGS. 3 to 5, an arrow 30 indicates coherent X-ray radiation that is provided by X-ray radiation, which has passed the source grating 54 (not shown). The radiation passes the slits 59 of the pre-collimator 55. The bars 57 provide a blocking of at least substantial attenuation of the X-ray radiation. As a result, radiation in form of a plurality of X-ray beam sections 32 displaced from each other by radiation-free sections 34 is provided. The radiation further passes the phase grating 58 and the analyzer grating 60 and finally reaches the detector segments 63 of the X-ray detector 62. Further, the calibration filter grating 10 is provided.

The calibration filter grating 10 is movable between a first, calibrating position $P_{CAL}$, in which the filter segments are arranged in the X-ray beam parts forming the plurality of X-ray beam sections 32, and a second, scanning position ($P_{IM}$), in which the filter segments are arranged out of the X-ray beam parts forming the plurality of X-ray beam sections 32 that are detected by the detector segments 63. The movement between the two positions is indicated with a double-arrow 65.

In FIGS. 3A, 4A and 5A, the calibration filter grating 10 is moved to the second, scanning position $P_{IM}$.

In FIGS. 3B, 4B and 5B, the calibration filter grating 10 is moved to the first, calibrating position $P_{CAL}$.

The examples of FIGS. 3 to 5 differ in the arrangement of the calibration filter grating 10 along the radiation direction.

In FIGS. 3A and 3B, the calibration filter grating 10 is arranged between the pre-collimator 55 and the phase grating 58.

In FIGS. 4A and 4B, the calibration filter grating 10 is arranged between the phase grating 58 and the analyzer grating 60.

In FIGS. 5A and 5B, the calibration filter grating 10 is arranged between the source grating 54 (not shown) and the pre-collimator 55.

The examples of FIGS. 3 to 5 also show a further aspect: The calibration filter grating 10 may be provided with a different thickness of the bars, i.e. a different width of the filter segments, and widths of the slits, i.e. a different width of the opening segments. In one example, the filter segments are provided with a width that is the same as the width of the X-ray beam sections, or only a bit larger, as shown in FIGS. 3A and 3B. In a second example, the filter segments are provided such that the resulting opening segments have the same width as the X-ray beam sections, or slightly larger than the X-ray beam sections, as shown in FIGS. 4A and 4B. In a third example, the filter segments and opening segments are provided with a similar or same width, as shown in FIGS. 5A and 5B. In all three cases the filter segments are sufficiently wide to provide the filtering of the respective X-ray beam section passing the filter segment in the filtering arrangement of the calibration filter grating 10. Further, in all three cases the opening segments are sufficiently wide to ensure that the respective X-ray beam section can pass the opening segments without having to pass filter material the imaging arrangement of the calibration filter grating 10, i.e. un-affected by the filter segment.

Figure 6:
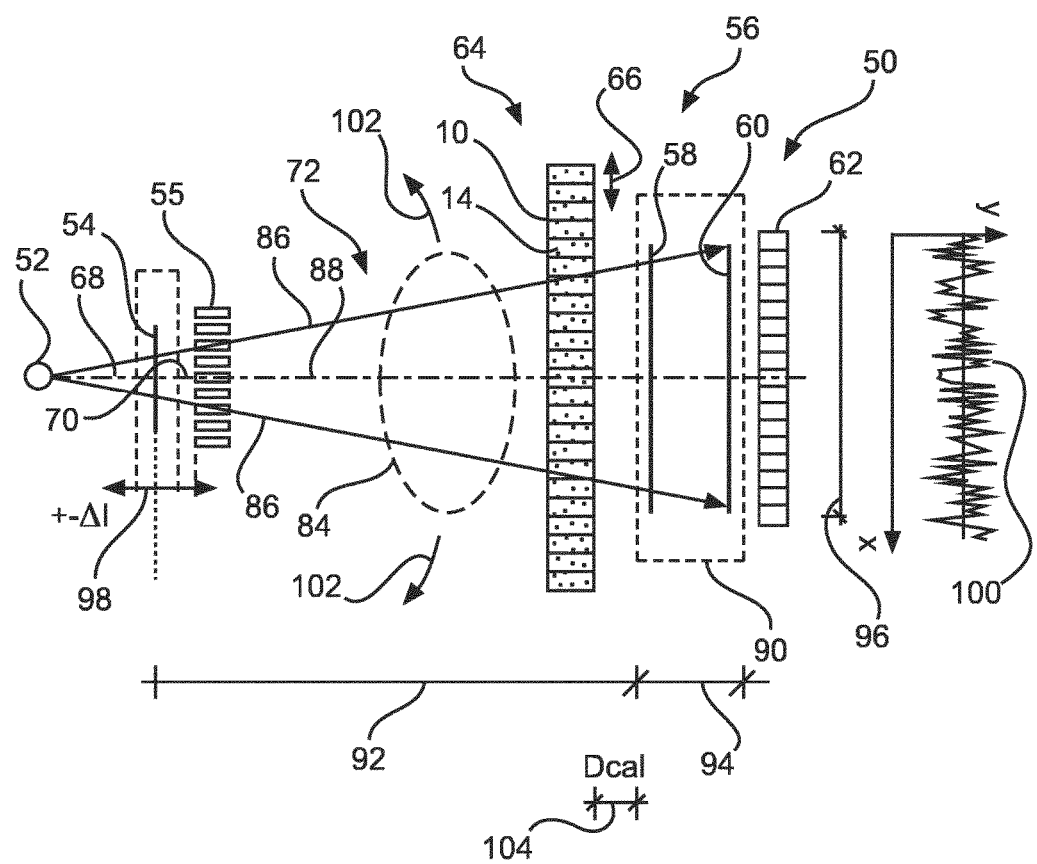
FIG. 6 shows a further example of a slit-scanning X-ray phase contrast imaging arrangement.

FIG. 6 shows a further example of the slit-scanning X-ray phase contrast imaging arrangement 50, wherein similar reference numerals are used for similar features. The X-ray radiation 68 is generated by an X-ray focus of the X-ray source 52. The X-ray radiation then passes the source grating 54 and the pre-collimator 55, and further passes through the region 72 for receiving the object or sample, indicated with a dotted line 84. The X-ray radiation beam width is indicated with two fan-shaped boundary lines 86 and a central axis line 88. Further, for calibration purposes, the filter segments 11 with the filter material 12 of the calibration filter grating 10 are provided in the X-ray beam parts forming the plurality of X-ray beam sections (while the object is not arranged in the X-ray beam) such that the X-ray radiation has to pass the filter segments 11 of the calibration filter grating 10 before reaching the phase grating 58 and the analyzer grating 60. A dotted line frame 90 indicates the interferometer unit 56. Finally, the detector 62 is reached.

Further, a distance 92 is indicated between the source grating 54, which source grating is also referred to as G0, and the phase grating 58, also referred to as G1. This distance 92 is also referred as distance L. A further distance 94 is indicated between the phase grating 58 and the analyzer grating 60, which further distance 94 is also referred to as distance D. Still further, a line 96 indicates a width W of the detector 62.

Still further, a movement $\pm \Delta L$ of the source grating 54 is indicated with arrows 98.

In case of scanning differential phase contrast imaging in the shown setup with the de-coherence filter 10 inserted into the X-ray pathway, the detector detects a signal that is graphically represented on the right side of the detector 62. A graph 100 indicates gain induced disturbances of detector flux. As can be seen, the Moiré fringe pattern is not visible, i.e. the Moiré fringe pattern is removed, and only signal fluctuations proportional to the individual pixel gain shows up at the detector 62. It must be noted that the graph 100 in reality is a discontinued graph with curve segments and missing segments, since the X-ray radiation from the X-ray source passes the pre-collimator 55 only in segments, i.e. in portions or pieces of X-ray radiation. Thus, only in these portions or segments radiation occurs that is filtered by the de-coherence filter and that will be detected. The discontinued graph 100 is shown in a continuous manner in FIG. 6 for illustrational reasons only. However, the discontinued graph will be explained in more detail also in relation with FIG. 7.

After the calibration steps, the calibration filter grating 10 is moved such that the filter segments 11 are arranged out of the X-ray beam parts forming the plurality of X-ray beam sections that are detected by the detector segments, and the object 84 can be arranged between the X-ray source, the X-ray source grating respectively, and the interferometer unit 56 for imaging purposes. For example, the sample can be moved laterally or rotationally, as indicated with arrows 102.

In an example, the application of the special de-coherence filter, i.e. the filter grating, is performed after scanning the object. In a further example, the application of the special de-coherence filter is performed also after the phase reference scan. In other words, the calibration scan is performed afterwards.

In a further example, the calibration filter grating 10 is arranged with a calibration distance $D_{cal}$ of approximately 5 to 10 mm from the phase grating 58. This example is shown in addition in FIG. 6, although provided as an option. The calibration distance $D_{cal}$ is indicated with reference numeral 104.

In a further example, not further shown in detail, the calibration filter grating 10 is arranged approximately half distance between the source grating G0 and the phase grating G1. In a further example, the calibration filter grating 10 is then provided with an increased filter thickness to at least partly compensate for the reduced filter strength.

The detected signal, as indicated with the graph 100, can then be used for determining a calibration factor representing the gain induced signal structure. This calibration factor can then be provided for calibration for further X-ray imaging procedures.

FIG. 7A) shows a first graph 106 with a detector signal distribution in scan direction without flat field correction. A first curve 108 is indicated, wherein a vertical axis 110 indicates the detected signal, and a horizontal line 112 indicates a detector pixel number. The first graph 106 is shown as a discontinued curve comprising curve segments 107 and missing segments 109, or gaps, since X-rays pass the pre-collimator only in segments, i.e. in portions or pieces of X-ray radiation, and not continuously over the whole width of the detector. Pairs of dotted lines 111 separating the curve segments 107 from the missing segments 109 are shown for illustration purposes only. FIG. 7B) shows a further graph 114 of the flat field reference signal distribution in scan direction in the presence of the calibration filter grating 10, i.e. in the presence of the de-coherent flat field filter. The vertical line 110 indicates the detected signal and the horizontal line 112 indicates the detector pixel number. As can be seen, a graph 116 is different from the graph 108. The further graph 114 is also shown as a discontinued graph with curve segments and missing segments (and dotted lines).

FIG. 7C) shows a further third graph 118 as a ratio of detector signals versus the flat field reference signal, wherein a vertical line 120 indicates the ratio of the detected signal versus the detector signal with the flat field reference signal, and a horizontal line 122 indicates the detector pixel number. Also, the further third graph 118 is shown as a discontinued graph with curve segments and missing segments (and dotted lines).

As can be seen from FIG. 7B), the Moiré fringes are removed, but the gain induced structure of the detector signal remains. In the following, i.e. in FIG. 7C), this flat field signal is used as reference signal in flat fielding pre-processing step by dividing all the subsequent detector signals pixel-wise by this reference. The result is displayed in the lower part in form of FIG. 7C). The Moiré fringes show up without pixel gain induced disturbances. It must be noted that photon induced noise due to photon statistics is neglected here.

FIG. 8 shows an X-ray imaging system 200, comprising an X-ray image acquisition arrangement 202, a processing device 204, and an object supporting device 206. The X-ray image acquisition arrangement 202 is provided as a slit-scanning X-ray phase contrast imaging arrangement 50, according to one of the above-mentioned examples. The object supporting device 206 is configured to support an object to be examined. The object is schematically indicated with an elliptic structure 208. The X-ray image acquisition arrangement is configured to detect an X-ray image signal as reference signal for calibration purposes, wherein the object 208 is arranged outside the X-ray radiation, which X-ray radiation is indicated with dotted lines 210. The processing unit is configured to determine a calibration factor based on the reference signal, wherein the calibration factor represents a gain induced signal structure. The processing unit 204 is further configured to provide the calibration factor for calibrated X-ray imaging procedures, as indicated with arrow 212 and a dotted line 214, entering the X-ray image acquisition arrangement 202. It must be noted that the slit-scanning X-ray phase contrast imaging arrangement 50 is indicated with a first frame 216, schematically representing the interferometer unit 56 together with the detector 62. A second frame 218 schematically represents the X-ray source 52 and the source grating 54.

A dotted frame 220 indicates the calibration device 64, i.e. the calibration filter grating 10, that can temporarily be arranged in the X-ray radiation for detecting the calibration signal in order to determine a calibration factor.

It must be noted that FIG. 8 shows the object 208 arranged in the X-ray radiation, and thus not the stage of recording a calibration signal. For calibration purposes, the object 208 will be removed, i.e. moved out of the X-ray radiation, and the calibration filter grating, i.e. the calibration device 64, will then be moved or arranged in the X-ray radiation.

Figure 9:
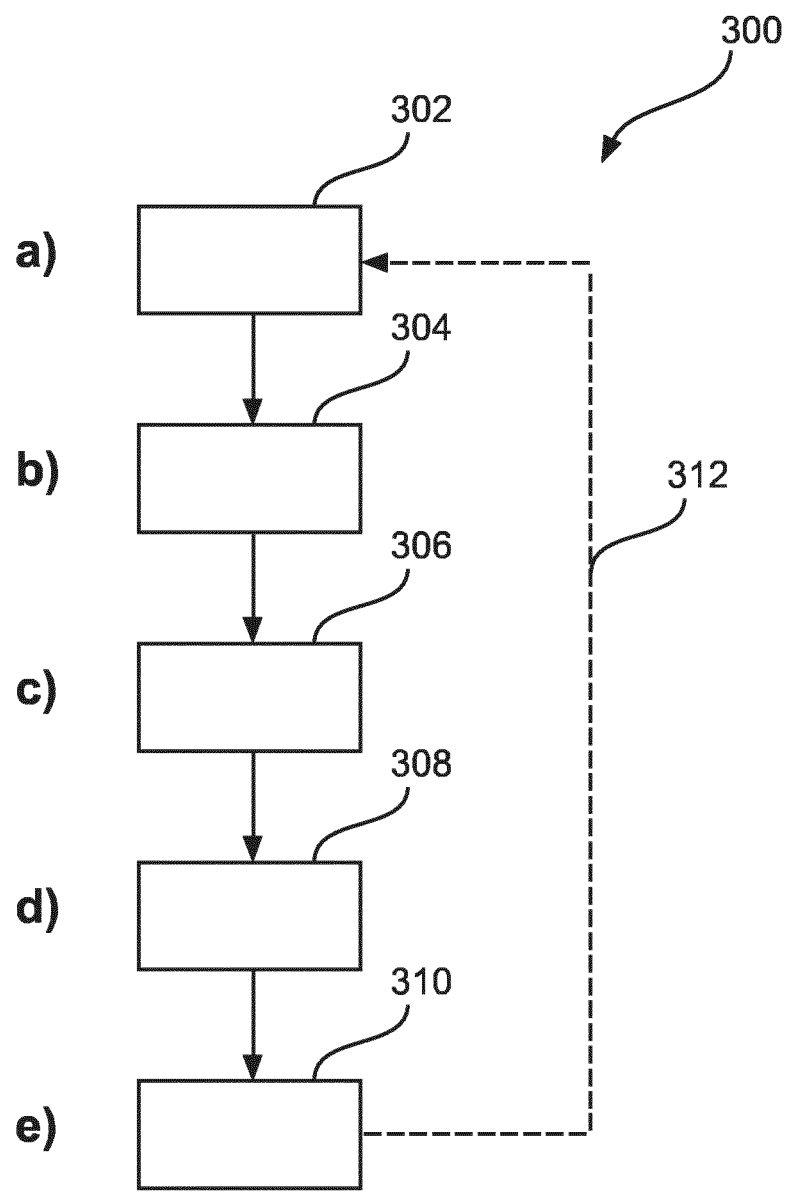
FIG. 9 shows an example of basic steps of a method for calibration in X-ray phase contrast imaging.

FIG. 9 shows a method 300 for calibration in X-ray phase contrast imaging. The method 300 comprises the following steps:

In an arranging step 302, a calibration filter is arranged in an X-ray beam of an X-ray image acquisition arrangement at a location between a source grating and a phase grating. The calibration filter is a calibration filter grating according to one of the above-mentioned examples.

In a first provision step 304, X-ray radiation is provided.

In a detection step 306, an X-ray image signal as reference signal is detected for calibration purposes.

In a determination step 308, a calibration factor is determined, based on the reference signal, wherein the calibration factor represents a gain induced signal structure.

In a second provision step 310, the calibration factor is then provided for calibrated X-ray imaging procedures.

The arrangement step 302 is also referred to as step a), the first provision step 304 as step b), the detection step 306 as step c), the determination step 308 as step d), and the second provision step 310 as step e).

In an example, in step e), the calibration factor is used to remove gain induced disturbances in next image acquisition steps.

According to a further example, the steps a) to d) are repeated before an object is arranged for a new image acquisition procedure. This further example is also shown in combination with FIG. 9 as an option, where the repetition is indicated with a loop-like arrow 312.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application.

However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A calibration filter grating for transforming coherent X-ray into incoherent X-ray in a slit-scanning X-ray phase contrast imaging arrangement, comprising:
   a first plurality of filter segments comprising a filter material; and
   a second plurality of opening segments;
   wherein the filter segments and the opening segments are arranged alternating as a filter pattern;
   wherein the filter material is made from a material with structural elements comprising structural parameters in the micrometer region; and
   wherein the filter grating is configured to be movably arranged between an X-ray source grating and an analyzer grating of an interferometer unit in a slit-scanning system of a phase contrast imaging arrangement; and
   wherein the filter pattern is configured to be aligned with a slit pattern of the slit-scanning system.

2. Calibration filter grating according to claim 1, wherein the structural elements are provided in a maximum range of 10 µm.

3. Calibration filter grating according to claim 1, wherein the filter material is provided as at least one of the group of:
   fluid bubbles comprising gaseous bubbles and liquid bubbles; and
   fiber-based material; and
   wherein the filter material is made from low atomic number elements.

4. Calibration filter grating according to claim 1, wherein the filter is a de-coherence filter providing small angle scattering for coherent X-ray radiation provided by an X-source with a source grating for phase contrast imaging.

5. A slit-scanning X-ray phase contrast imaging arrangement, comprising:
   an X-ray source;
   a source grating;
   a pre-collimator;
   an interferometer unit comprising a phase grating and an analyzer grating;
   an X-ray detector with a plurality of detector segments displaced from each other; and
   a calibration device;
   wherein the source grating provides at least partially coherent X-ray radiation;
   wherein the pre-collimator comprises a plurality of bars and slits to provide an X-ray beam width with a plurality of X-ray beam sections displaced from each other by radiation-free sections;
   wherein the calibration device is a calibration filter grating according to one of the preceding claims; and
   wherein the calibration filter grating is arranged between the source grating and the analyzer grating; and
   wherein the calibration filter grating is movable between:
   I) a first, calibrating position, in which the filter segments are arranged in the X-ray beam parts forming the plurality of X-ray beam sections; and
   II) a second, scanning position, in which the filter segments are arranged out of the X-ray beam parts forming the plurality of X-ray beam sections that are detected by the detector segments.

6. Slit-scanning X-ray phase contrast imaging arrangement according to claim 5, wherein, the calibration filter grating is arranged:
   i) between the source grating and the pre-collimator; or
   ii) between the pre-collimator and the phase grating; or
   iii) between the phase grating and the analyzer grating.

7. Slit-scanning X-ray phase contrast imaging arrangement according to claim 5, wherein in the scanning position, the calibration filter grating remains between the source grating and the analyzer grating; and wherein the filter segments are arranged in the radiation-free sections of the X-ray beam or in the X-ray beam parts that are blocked by bars of the pre-collimator.

8. Slit-scanning X-ray phase contrast imaging arrangement according to claim 5, wherein the phase grating is provided with a first period; and
   wherein the structures of the structural elements are provided in a range of approximately the first period.

9. Slit-scanning X-ray phase contrast imaging arrangement according to claim 5, wherein a displacement device for moving the calibration filter grating between the first, calibrating position and the second, scanning position is provided.

10. Slit-scanning X-ray phase contrast imaging arrangement according to claim 9, wherein the displacement device is provided as at least one of the group of:
- a motor driven translation stage;
- a electromagnetic actuation stage; and
- a piezoelectric translation stage.

11. An X-ray imaging system, comprising:
an X-ray image acquisition arrangement;
a processing device; and
an object supporting device;
wherein the X-ray image acquisition arrangement is provided as a slit-scanning X-ray phase contrast imaging arrangement according to claim 5;
wherein the object supporting device is configured to support an object to be examined;
wherein the X-ray image acquisition arrangement is configured to detect an X-ray image signal as reference signal for calibration purposes, wherein an object is arranged outside the X-ray radiation; and
wherein the processing unit is configured to determine a calibration factor based on the reference signal, wherein the calibration factor represents a gain induced signal structure; and to provide the calibration factor for calibrated X-ray imaging procedures.

12. X-ray imaging system according to claim 11, wherein the filter segments of the calibration device are configured to be arranged in the X-ray beam parts forming the X-ray beam sections for calibration purposes and outside the X-ray beams parts forming the X-ray beam sections for object and phase reference acquisition steps.

13. A computer program element for controlling an apparatus claim 1, which, when being executed by a processing unit, is adapted to perform the method for calibration in slit-scanning X-ray phase contrast imaging, comprising the following steps:
   a) arranging a first plurality of filter segments of a calibration filter grating, for transforming coherent X-ray into incoherent X-ray, in X-ray beam parts forming X-ray beam sections of an X-ray image acquisition arrangement at a location between a source grating and an analyzer grating; the filter segments comprise a filter material made from a material with structural elements comprising structural parameters in the micrometer region;
   b) providing X-ray radiation;
   c) detecting an X-ray image signal as reference signal for calibration purposes;
   d) determining a calibration factor based on the reference signal, wherein the calibration factor represents a gain induced signal structure; and
   e) providing the calibration factor for calibrated X-ray imaging procedures.

14. A computer readable medium having stored the program element of claim 13.

* * * * *